US006448275B2

(12) United States Patent
Young

(10) Patent No.: US 6,448,275 B2
(45) Date of Patent: *Sep. 10, 2002

(54) METHODS FOR TREATING HYPERTENSION AND ANGINA USING SALTS OF OPTICALLY PURE (-) AMPLODIPINE

(75) Inventor: James W. Young, Palo Alto, CA (US)

(73) Assignee: Sepracor Inc., Marlborough, MA (US)

( * ) Notice: Subject to any disclaimer, the term of this patent is extended or adjusted under 35 U.S.C. 154(b) by 98 days.

This patent is subject to a terminal disclaimer.

(21) Appl. No.: 09/840,117

(22) Filed: Apr. 24, 2001

Related U.S. Application Data

(63) Continuation of application No. 09/523,733, filed on Mar. 13, 2000, now Pat. No. 6,291,490, which is a continuation of application No. 08/334,771, filed on Nov. 4, 1994, now Pat. No. 6,057,344, which is a continuation of application No. 07/981,562, filed on Nov. 25, 1992, now abandoned, which is a continuation of application No. 07/798,466, filed on Nov. 26, 1991, now abandoned.

(51) Int. Cl.$^7$ .............................................. A61K 31/44
(52) U.S. Cl. ...................................................... 514/356
(58) Field of Search ......................................... 514/356

(56) References Cited

U.S. PATENT DOCUMENTS

| | | | |
|---|---|---|---|
| 4,572,909 A | 2/1986 | Campbell et al. | ............ 514/356 |
| 4,806,557 A | 2/1989 | Campbell et al. | ............ 514/356 |
| 4,879,303 A | 11/1989 | Davison et al. | ............. 514/356 |
| 5,155,120 A | * 10/1992 | Lazar et al. | |

FOREIGN PATENT DOCUMENTS

| | | |
|---|---|---|
| EP | 0 089 167 A2 | 9/1983 |
| EP | 0 331 315 A2 | 9/1989 |
| JP | 1-156959 | 6/1989 |

OTHER PUBLICATIONS

Goldmann, S. et al., "Determination of the Absolute Configuration of the Active Amlodipine Enantiomer as (-)-S: A Correction", *Journal of Medicinal Chemistry* 35(18):3341–3344 (1992).
Alker, D. et al., "Long–acting dihydropyridine calcium antagonists. 9. Structure Activity Relationships Around Amlodipine", *Eur. J. Med. Chem.* 26: 907–913 (1991).
Basco, L.K. and Le Bras, J., "Plasmodium falciparum: In Vitro Drug Interaction between Chloroquine and Enantiomers of Amlodipine", *Experimental Parasitology* 72: 262–270 (1991).
Deloron, P. et al., "In Vitro and In Vivo Potentiation of Chloroquine against Malaria Parasites by an Enantiomer of Amlodipine", *Antimicrobial Agents and Chemotherapy* 35(7): 1338–1342 (1991).
Eriksson, U.G. et al., "Stereoselective Metabolism of Felodipine in Liver Microsomes from Rat, Dog, and Human", *Drug Metabolism and Disposition* 19(5):889–894 (1991).

Goldmann, S. and Stoltefuss, J., "1,4–Dihydropyrdines: Effects of Chirality and Conformation on the Calcium Antagonist and Calcium Agonist Activities", *Angew. Chem. Int. Ed. Engl.* 30: 1559–1578 (1991).
Nayler, W.G. and Gu, X.H., "(-)[$^3$H]Amlodipine Binding to Rat Cardiac Membranes", *Journal of Cardiovascular Pharmacology* 17: 587–592 (1991).
Okamoto, Y. et al., "Optical resolution of dihydropyridine enantiomers by high–performance liquid chromatography using phenylcarbamates of polysaccharides as a chiral stationary phase", *Journal of Chromatography* 513: 375–378 (1990).
Soons, P.A. et al., "Enantioselective Determination of Felodipine and Other Chiral Dihydropyridine Calcium Entry Blockers in Human Plasma", *Journal of Chromatography* 528: 343–356 (1990).
Abernethy, L, "The Pharmacokinetic Profile of Amlodipine", *American Heart Journal* 1100–1103 (1989).
Glasser, S.P. et al., "Safety and Efficacy of Amlodipine Added to Hydrochlorothiazide Therapy in Essential Hypertension", *American Journal of Hypertension, Inc.* 2(3)(1): 154–157 (1989).
*The Merck Index*, Eleventh Edition, Monograph 509 (1989).
Osterloh, I., "The safety of amlodipine", *American Heart Journal* 1114–1120 (1989).
Isenring, H.P., "Antifungal Morpholine Derivatives: Chemistry and Structure–Activity Relationships", *Recent Trends in the Discovery, Development and Evaluation of Antifungal Agents,*–R.A. Fromtling (Ed.), J.R. Prous Science Publishers, S.A., pp. 543–554 (1987).
Arrowsmith, J.E. et al., "Long–Acting Dihydropyridine Calcium Antagonists. 1.2–Alkoxymethyl Derivatives Incorporating Basic Substituents", *J. Med. Chem.* 29: 1696–1702 (1986).
A.R. Gennaro, Ed., "Remington's Pharmaceutical Sciences, 18th Ed." published by Mack Published Co. (Easton, PA), pp. 853–854 (1990).
Ariens, E.J., "Stereoselectivity in Pharmacodynamics and Pharmacokinetics", *Schweiz. Med. Wochenschr.* 120: 131–134 (1990).
Ariens, E.J., "Racemic Therapeutics—Ethical and Regulatory Aspects", *Eur. J. Clin. Pharmacol.* 41: 89–93 (1991).

(List continued on next page.)

Primary Examiner—William R. A. Jarvis
(74) Attorney, Agent, or Firm—Pennie & Edmonds LLP

(57) ABSTRACT

Methods and compositions are disclosed utilizing the optically pure (-) isomer of amlodipine. This compound is a potent drug for the treatment of hypertension while avoiding the concomitant liability of adverse effects associated with the racemic mixture of amlodipine. The (-) isomer of amlodipine is also useful for the treatment of angina and such other conditions as may be related to the activity of (-) amlodipine as a calcium channel antagonist such as cerebral ischemia, cerebral disorders, arrhythmias, cardiac hypertrophy, coronary vasospasm, myocardial infarction, renal impairment and acute renal failure, without the concomitant liability of adverse effects associated with the racemic mixture of amlodipine.

52 Claims, No Drawings

OTHER PUBLICATIONS

J. Luksa et al., "Pharmacokinetic Behaviour of R–(+)–and S–(–)–Amlodipine After Single Enantiomer Administration," *Journal of Chromatography B*, 703:185–193 (1997).

H. Laufen et al., "Enantioselective Disposition of Oral Amlodipine in Healthy Volunteers," *Chirality*, 6:531–536 (1994).

* cited by examiner

METHODS FOR TREATING HYPERTENSION AND ANGINA USING SALTS OF OPTICALLY PURE (−) AMPLODIPINE

This is a continuation of application No. 09/523,733, filed Mar. 13, 2000, now U.S. Pat. No. 6,291,490 which is a continuation of application No 08/334,771, filed Nov. 4, 1994, now U.S. Pat. No. 6,057,344, which is a continuation of application No. 07/981,562, filed Nov. 25, 1992, now abandoned, which is a continuation of application No. 07/798,466, filed Nov. 26, 1991, now abandoned.

1. BACKGROUND OF THE INVENTION

This invention relates to novel compositions of matter containing optically pure (−) amlodipine. These compositions possess potent activity in treating both systolic and diastolic hypertension while avoiding adverse effects including but not limited to edema of the extremities, headache and dizziness, which are associated with administration of the racemic mixture of amlodipine. Additionally, these novel compositions of matter containing optically pure (−) amlodipine are useful in treating angina and such other conditions as may be related to the activity of (−) amlodipine as a calcium channel antagonist including but not limited to cerebral ischemia, cerebral disorders, arrhythmias, cardiac hypertrophy, coronary vasospasm, myocardial infarction, renal impairment and acute renal failure ——while avoiding the adverse effects associated with administration of the racemic mixture of amlodipine. Also disclosed are methods for treating the above-described conditions in a human while avoiding the adverse effects that are associated with the racemic mixture of amlodipine, by administering the (−) isomer of amlodipine to said human.

1.1. Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been thought to be a potent teratogen.

The active compound of this composition and method is an optical isomer of the compound amlodipine, which is described in Campbell et al., U.S. Pat. No. 4,572,909. Chemically, this (−) isomer is 3-ethyl 5-methyl (−)-2-[(2-aminoethoxy) methyl]-4-(2-chlorophenyl)-1,4-dihydro-6-methyl-3,5-pyridine-dicarboxylate. This isomer will hereinafter be referred to as (−) amlodipine. (−) amlodipine also includes the substantially optically pure (−) amlodipine isomer.

Amlodipine, which is the subject of the present invention, is available commercially only as the 1:1 racemic mixture. That is, it is available only as the 1:1 mixture of optical isomers, called enantiomers. The racemic mixture of amlodipine that is commercially available for administration is a besylate salt.

1.2. Pharmacologic Action

The racemic mixture of amlodipine is in the class of compounds known as calcium antagonists. The concept of a specific mechanism of pharmacologic action related to the antagonism of calcium movement in the process of excitation-contraction was suggested by Fleckenstein et. al. (see Fleckenstein, A., *Calcium Antagonism in Heart and Smooth Muscle:Experimental Facts and Therapeutic Prospects,* New York, Wiley, 1983; Swamy, V. and D. Triggle, *Modern Pharmacology,* 2nd. Ed., Craig and Stitzel, Eds., Little, Brown and Co., Boston, 1986, Chapt. 26, 373–380; Triggle, D. J., and R. A. Janis, *Ann. Rev. Pharm. and Tox.* 27: 347–369, 1987). Many of the currently available calcium antagonists appear to antagonize the entry of calcium through voltage dependent channels in the plasma membrane of cells. The pharmacologic class of calcium antagonists consists of chemically diverse compounds. Given the structural heterogeneity of the class it is likely that the pharmacological action involves more than one site or mechanism of action.

Amlodipine is one of a series of dihydropyridine calcium antagonists. However, amlodipine has a generally slower onset and longer duration of action than, for example, nifedipine. (Jensen, H. et al., *J. Hum. Hypertens.,* 42(5): 541–45, 1990). The metabolites of amlodipine apparently do not possess significant calcium channel blocking activity, while the parent drug offers a biological half-life of some 35–40 hours, prompting a once-daily dosage regimen. (Lorimer, A. R., et al., *J. Hum. Hypertens.,* 3(3): 191–96, 1989; Glasser, S. F. et al., *AJH,* 2(3): 154–57, 1989). Its ability to block, calcium channels in smooth muscle produces peripheral vasodilation resulting in decreases in both systolic and diastolic blood pressure.

With regard to the enantiomers of amlodipine, these are disclosed in Arrowsmith et al. *J. Med. Chem.,* 29: 1696–1702 (1986). This reference discusses in vitro tests to determine calcium antagonist activity against calcium-induced constriction of potassium-depolarized rat aorta. The authors allege that in vitro evaluation of the enantiomers of amlodipine shows the (−) isomer to be twice as active as the racemic mixture in antagonizing calcium-induced constriction of potassium-depolarized rat aorta. The authors also allege that the (+) isomer of amlodipine is some 1,000 times less active in these in vitro tests. Further, European Patent Application No. 0 331 315 discloses a method for separation of the R(−) and S(+) isomers of amlodipine. While these references discuss the enantiomers of amlodipine, they only provide a method of synthesis and in vitro test results of the individual enantiomer activity as found in rat aorta. There is no disclosure of the effects of or a suggestion for administering one of the enantiomers of amlodipine to a human. Moreover, there is no disclosure or suggestion of the alleviation or reduction of side effects which is achieved by the administration of (−) amlodipine.

The racemic mixture of amlodipine is presently used primarily as an antihypertensive agent; it is generally taken orally as a once-daily therapy. As stated above, the racemic mixture of amlodipine produces peripheral vasodilation, resulting in decreases in both systolic and diastolic blood pressure when used as an antihypertensive agent. This antihypertensive effect occurs in the relative absence of significant or sustained effects on cardiac rate.

While yet the subject of extensive research, hypertension appears to be the product of an inherited predisposition—coupled with dietary, emotional, and environmental factors, which results in a structural adaptation of the cardiac muscle and the large blood vessels. Most patients display heightened vascular and cardiac reactions to sympathetic nervous stimulation, but the precise relationship of sympathetic nervous stimulation to the etiology of the disease. Nevertheless, hypertension results in chronic readjustment of cardiovascular hemodynamics, alteration of blood vessel walls, cardiovascular resistance and regional transmural pressures.

Pharmacologic management of hypertension is generally directed to the normalization of altered hemodynamic parameters, and many drugs and drug classes, either as monotherapy or in combination treatment, can reduce and control elevated blood pressure. However, treatment of hypertension does not always correspondingly benefit the morbidity and mortality of the condition, either because chronic hypertension has produced other significant and irreversible cardiovascular changes, or because present drugs have an adverse effect on some other risk factor for cardiovascular disease. Rather, current drug therapy simply provides sustained arterial pressure reduction.

Furthermore, the racemic mixture of amlodipine is useful in treating other disorders such as angina pectoris.

Angina pectoris is a highly variable, rather poorly understood clinical syndrome reflecting a myocardial ischemia. When cardiac work or myocardial oxygen demand exceeds the ability of the coronary arterial vascular system to supply oxygen, the resulting ischemia stimulates the sensory nerves of the heart, producing the sensation of angina characterized by episodes of precordial pressure, discomfort, or a severe, intense crushing pain which may radiate to several sites including the left shoulder and left arm. Physical activity or exertion characteristically initiates the condition, and rest or drug therapy relieves the condition. The signs and symptoms of an episode persist for a few minutes, but can be induced or exaggerated by a meal or exposure to cold air. Treatment is directed to the underlying disease, usually atherosclerosis, or to drugs which either reduce myocardial oxygen demand or improve oxygen supply. Calcium antagonists such as amlodipine have been particularly useful in treating vasospastic angina, the angina of effort, and the unstable angina, due to the effect of the calcium channel antagonist on cardiac and vascular smooth muscle.

Amlodipine may be useful in the treatment of cerebral ischemia. Cerebral ischemia, often the result of atherosclerotic disease or hypertension, results from insufficient cerebral circulation. Under normal circumstances, an extensive collateral circulation ensures adequate blood flow. However, cerebral ischemia may result from either an intra- or extracranial interruption of arterial blood flow. If interruption is transient, the cerebral tissues recover, and neurologic symptoms disappear. If the ischemia lasts for a somewhat more extended period, infarction results and the resulting neurologic damage is permanent. In the case of extended ischemia. resulting in infarction, treatment is directed to the underlying vascular disease, to blood platelet aggregation inhibitors, and anticoagulant therapy.

Because of its activity as a calcium channel antagonist, amlodipine may also be useful in treating cardiac arrhythmias. Cardiac arrhythmias represent a broad, complex group of electrophysiologic disorders that affect the mechanical properties of the heart and vasculature, altering normal cardiac rhythm, function and output. Normal cardiac rhythm originates with the sinoatrial node, which possesses high intrinsic automaticity. Adequate automaticity and conduction lead to activation of atrial and ventricular fibers, producing in sequence the elements of normal functional heart beat. Calcium antagonists may be of value in conditions where calcium-related changes in membrane potential and conduction alter normal rhythm. In the absence of treatment, symptoms vary with individual arrhythmias, but are often the consequence of inadequate cardiac filling and output and often include fatigue, decreased exercise tolerance, syncope, shortness of breath, nausea, lightheadedness and the like.

Amlodipine may be useful to treat cardiac hypertrophy. Cardiac hypertrophy can result from excessive workload either due to an obstruction to outflow, termed systolic overload, or to excessive volumes presented to the heart in diastole, termed diastolic overload. Systolic overload results in concentric ventricular hypertrophy, in which there is an increased thickness in the walls of the heart not associated with increased volume. Diastolic overload causes dilation and hypertrophy with an increased blood volume. An inadequate cardiac output results from the heart's failure in systolic or diastolic overload, leading to fatigue, shortness of breath, pulmonary congestion, edema and the like. Calcium channel antagonists effect workload and, as such, may be useful in treating cardiac hypertrophy due to the effect of the calcium antagonist on cardiac and vascular smooth muscle in reducing blood pressure.

It is also possible that amlodipine could be used to treat coronary arterial spasm. Coronary arterial spasm can occur in the absence of significant coronary atherosclerosis and is thought to be an initiating event in variant angina and in myocardial infarction. Coronary spasm may occur without the patient feeling any significant discomfort. In an electrically unstable heart, diverse neural impulses to the heart may provoke coronary vascular spasm. This may result in enhanced myocardial ischemia and arrhythmia, which in turn may culminate in ventricular fibrillation and sudden cardiac death. As in variant or vasospastic angina, the calcium channel antagonists may be of particular usefulness due to their effect on cardiac and vascular smooth muscle.

Furthermore, amlodipine may be useful in the treatment of myocardial infarction, ischemic myocardial necrosis, and ischemia reperfusion injury. Myocardial infarction or ischemic myocardial necrosis generally results from the abrupt reduction of coronary blood flow to a portion of the myocardium The condition likely originates from atherosclerosis of the coronary arteries. Either coronary artery vasospasm or acute coronary thrombosis precipitates the condition, although the etiology is the subject of continuing research. Myocardial infarction is predominantly a disease of the left ventricle. Precordial pain and left ventricular dysfunction characterize the disease. The pain, which can be severe aching or pressure, leads to apprehension. Symptoms include left ventricular heart failure, pulmonary edema, shock or significant cardiac arrhythmia. Calcium channel antagonists may find utility in the management of myocardial infarction patients due to their effects on coronary artery vasospasm, blood pressure or other effects on cardiac function or vascular smooth muscle.

Amlodipine may be used to treat congestive heart failure. Congestive heart failure can be caused by hypertension, cardiomyopathy, coronary artery disease or valvular heart disease. Congestive failure results in poor cardiac output and elevated left-ventricular diastolic pressure, leading to dyspnea, fatigue, peripheral edema, and coughing. The ability of some calcium antagonists to lower afterload by dilating peripheral arteries without having a significant inotropic effect may increase their use in treating congestive heart failure.

Amlodipine may be of use in treating migraine. Classic migraine typically begins with visual auras followed by severe headaches, often accompanied by nausea and vomiting. Common migraine has similar symptoms without the preceding visual aura. The causes of migraine have been studied intensely, and are still a matter of debate. The most generally accepted cause is hypoxia due to reduced cerebral blood flow. Calcium channel antagonists have been used for migraine prophylaxis since they can increase cerebral blood flow.

Amlodipine may also be useful for treating Raynaud's phenomenon, which is characterized by vascular spasm of the extremities. These vasospasms can be caused by cold or stress. A pallor or cyanosis is usually present due to severe constriction of the digital arteries. The phenomenon is often seen as a secondary disorder with arterial diseases or connective tissue diseases such as scleroderma, arthritis or lupus erythematosus. Calcium channel antagonists have been shown to be effective in treating Raynaud's phenomenon.

Amlodipine may be useful in the treatment of asthma and bronchospasm. Symptoms of asthma—coughing, wheezing, and dyspnea—are caused by constriction of tracheobronchial smooth muscle. Asthma attacks can be triggered by antigenic stimuli (pollen, dust) or non-antigenic stimuli (exercise, pollution, infection). The response to these stimuli lead to secretions of chemical mediators that cause smooth muscle contraction. Calcium channel antagonists can be used to control bronchoconstriction and relieve asthma attacks.

In addition, the racemic mixture of amlodipine may be useful to treat renal impairment and acute renal failure. Renal impairment and acute renal failure are clinical conditions of diverse etiology, which are associated with an increasing azotemia or urea nitrogen in the blood, and often an oliguria or a diminished volume of urine in relation to fluid intake. The pathophysiology may originate prerenally, manifest as inadequate renal perfusion, due to extracellular fluid volume depletion or cardiac failure. The most common cause of intrinsic renal failure is prolonged renal ischemia. Postrenal azotemia may be associated with obstruction or renal glomerular and tubular dysfunction. Laboratory findings disclose progressive azotemia, acidosis, hyperkalemia, and hyponatremia. Factors aggravating kidney impairment or failure must be specifically treated, including heart failure, obstruction and the like. Moderate or severe hypertension has a deleterious effect on renal function, and management of the hypertension with a variety of drugs including calcium channel antagonists may be useful therapy.

In addition, the racemic mixture of amlodipine could be useful in the treatment of cognitive disorders. Cognitive disorders include but are not limited to dementia and age-associated memory impairment.

Dementia can occur at any age. It is a structurally caused permanent or progressive decline in several dimensions of intellectual function that interferes substantially with individual normal social or economic activity.

One particular type of dementia is Alzheimers-type dementia. Alzheimers-type of dementia is thought to be due to a degenerative process, with a large loss of cells from the cerebral cortex and other brain areas. Acetylcholine-transmitting neurons and their target nerve cells are particularly affected. The brain shows marked atrophy with wide sulci and dilated ventricles. Senile plaques and neurofibrillary tangles are present. Memory loss is the most prominent early symptom. Disturbances of arousal do not occur early in the course. Alzheimer's presenile and senile onset dementias are similar in both clinical and pathologic features, with the former commonly beginning in the 5th and 6th decades and the latter in the 7th and 8th decades. The dementia usually progresses steadily, becoming well advanced in 2 to 3 years. Some cases of dementia occurring in the presenile period are hard to classify and are sometimes labelled idiopathic or simple presenile dementia.

The signs and symptoms of dementia in particular Alzheimers-type dementia include depression, paranoia, anxiety or any of several other psychologic symptoms. The most common clinical picture is slow disintegration of personality and intellect due to impaired insight and judgment and loss of affect. Memory impairment increases, beginning with problems recalling recent events or finding names. The impairment varies greatly from time to time and often from moment to moment. Dementia generally is an insidious, slowly progressive, untreatable condition. However, the rate of progression varies widely and depends on the cause.

Another type of cognitive disorder is age-associated memory impairment (AAMI). AAMI is used to describe healthy non-demented people who have experienced memory loss over the course of the person's life. Most commonly it is used to describe adults over the age of 50 who have experienced memory loss over the course of adult life. It has been estimated that between 25% and 50% of people over the age of 65 have this disorder.

Many calcium channel antagonists cause significant adverse effects. These adverse effects include but are not limited to tachycardia, orthostatic hypotension and fluid retention. In contrast to the situation with several other calcium channel antagonists, however, the racemic mixture of amlodipine has not been found to cause either marked or prolonged direct effects on heart rate or the reflex consequence of vasodilation.

However, the administration of the racemic mixture of amlodipine to a human has been found to cause still other adverse effects. These adverse effects include but are not limited to edema of, the extremities including peripheral edema, headache, flushing/hot flashes, fatigue, vertigo, muscle cramps and dizziness.

Thus, it would be particularly desirable to find a compound with the advantages of the racemic mixture of amlodipine which would not have the aforementioned disadvantages of significant adverse side effects and which was useful for treatment of other conditions.

2. SUMMARY OF THE INVENTION

It has now been discovered that the optically pure (−) isomer of amlodipine is an effective antihypertensive agent for both systolic and diastolic hypertension, particularly in mild to moderate disease and angina, while avoiding adverse effects including but not limited to edema of the extremities, headache and dizziness, which are associated with the administration of the racemic mixture of amlodipine. It has also been discovered that these novel compositions of matter containing optically pure (−) amlodipine are useful in treating other conditions as may be related to the activity of (−) amlodipine as a calcium channel antagonist, including but not limited to cerebral ischemia, cerebral disorders, arrhythmias, cardiac hypertrophy, coronary vasospasm, myocardial infarction, renal impairment and acute renal failure while avoiding the above-described adverse effects associated with the administration of the racemic mixture of amlodipine. The present invention also includes methods for treating the above-described conditions in a human while avoiding the adverse effects that are associated with the racemic mixture of amlodipine by administering the (−) isomer of amlodipine to said human.

3. DETAILED DESCRIPTION OF THE INVENTION

The present invention encompasses a method of eliciting an antihypertensive effect in a human, while avoiding the concomitant liability of adverse effects, which comprises administering to said human in need of such antihypertensive therapy, an amount of (−) amlodipine or a pharmaceutically acceptable salt thereof, substantially free of its (+) stereoisomer, said amount being sufficient to alleviate hypertension, but insufficient to cause said adverse effects associated with administration of racemic amlodipine.

The present invention also encompasses an antihypertensive composition for the treatment of a human in need of antihypertensive therapy, which comprises an amount of (−) amlodipine or a pharmaceutically acceptable salt thereof, substantially free of its (+) stereoisomer, said amount being sufficient to alleviate said hypertension but insufficient to cause adverse effects of racemic amlodipine.

The present invention further encompasses a method of treating angina in a human, while avoiding the concomitant liability of adverse effects, which comprises administering to said human in need of such anti-angina therapy, an amount of (−) amlodipine, or a pharmaceutically acceptable salt thereof, substantially free of its (+) stereoisomer, said amount being sufficient to alleviate said condition but insufficient to cause said adverse effects associated with administration of racemic amlodipine.

In addition, the present invention encompasses an antianginal composition for the treatment of a human having angina, which comprises an amount of (−) amlodipine or a pharmaceutically acceptable salt thereof, substantially free of its (+) stereoisomer, said amount being sufficient to alleviate said angina but insufficient to cause adverse effects of racemic amlodipine.

A further aspect of the present invention includes a method of treating a condition caused by excessive calcium influx in cells in a human, while avoiding the concomitant liability of adverse effects, which comprises administering to said human in need of a reduction in excessive calcium influx an amount of (−) amlodipine, or a pharmaceutically acceptable salt thereof, substantially free of its (+) stereoisomer, sufficient to alleviate said condition but insufficient to cause said adverse effects of racemic amlodipine. Conditions caused by excessive calcium influx in cells in a human include but are not limited to cerebral ischemia, cerebral disorders such as cognitive disorders including but not limited to Alzheimer's dementia and memory impairment, arrhythmias, cardiac hypertrophy, congestive heart failure, coronary vasospasm, migraine, bronchospasm and asthma, Raynaud's phenomenon, myocardial infarction, renal impairment and acute renal failure.

Furthermore, the present invention includes a composition for treating a condition caused by excessive calcium influx in cells in a human, which comprises an amount of (−) amlodipine, or a pharmaceutically acceptable salt thereof, substantially free of its (+) stereoisomer, said amount being sufficient to alleviate said condition but insufficient to cause adverse effects of racemic amlodipine.

The commercially available racemic mixture of amlodipine (e.g., a 1:1 racemic mixture of the two enantiomers) causes antihypertensive and antianginal activity; however, this racemic mixture, while offering the expectation of efficacy, causes adverse effects. Utilizing the (−) isomer of amlodipine results in clearer dose-related definitions of efficacy, surprisingly diminished adverse effects, and accordingly, an improved therapeutic index. It is, therefore, more desirable to use the (−) isomer of amlodipine.

The term "adverse effects" includes, but is not limited to, cardiovascular effects (including tachycardia and diminished contractility of the heart), edema of the extremities, headache, dizziness, flushing, fatigue, vertigo, and muscle cramps.

The term "substantially free of its (+) stereoisomer" as used herein means that the composition contains a greater proportion or percentage of the (−) isomer of amlodipine in relation to the (+) isomer of amlodipine, said percentage being based on the total amount of amlodipine. In a preferred embodiment the term "substantially free of its (+) stereoisomer" means that the composition contains at least 90% by weight of (−) amlodipine, and 10% by weight or less of (+) amlodipine. In the most preferred embodiment the term "substantially free of the (+) stereoisomer" means that the composition contains at least 99% by weight (−) amlodipine, and 1% or less of (+) amlodipine. In another preferred embodiment the term "substantially free of its (+) stereoisomer" as used herein means that the composition contains 100% by weight of (−) amlodipine. The terms "substantially optically pure (−) isomer of amlodipine are also encompassed by the above-described meanings.

The term "eliciting an antihypertensive effect" as used herein means providing a normalization to otherwise elevated systolic and/or diastolic blood pressure, and by so doing providing relief from any possible symptoms or other hemodynamic effects caused by the elevated pressure.

The term "a method of treating angina" as used herein means relief from the symptoms of myocardial ischemia, which include, but are not limited to, episodes of precordial pressure, discomfort, or a severe intense, crushing pain which may radiate, and which may be accompanied by changes in respiration, pulse rate, and blood pressure.

The term, "a condition caused by excessive calcium influx in cells in a human" includes but is not limited to conditions involving calcium influx in human cell that may be present in smooth muscle, cardiac, and other tissues including lung and brain. These conditions include, but are not limited to, cerebral ischemia, cerebral disorders such as cognitive disorders including Alzheimer's dementia and memory impairment, arrhythmias, cardiac hypertrophy,, congestive heart failure, coronary vasospasm, migraine, bronchospasm and asthma, Raynaud's phenomenon, myocardial infarction, renal impairment and acute renal failure. The symptoms associated with these disorders include, but are not limited to, the symptoms of precordial discomfort or pain, headache, fatigue, decreased exercise tolerance, syncope, shortness of breath, nausea, lightheadedness, edema, pulmonary congestion, arrhythmia or palpitation, azotemia, and/or oliguria.

The chemical synthesis of the racemic mixture of amlodipine can be performed by the method described in Arrowsmith, J. E. et al., *J. Med. Chem.,* 29: 1696–1702 (1986).

A technique for separation of the amlodipine isomers from the racemic mixture is illustrated schematically (see Arrowsmith, J. E. EP 331,315) as follows:

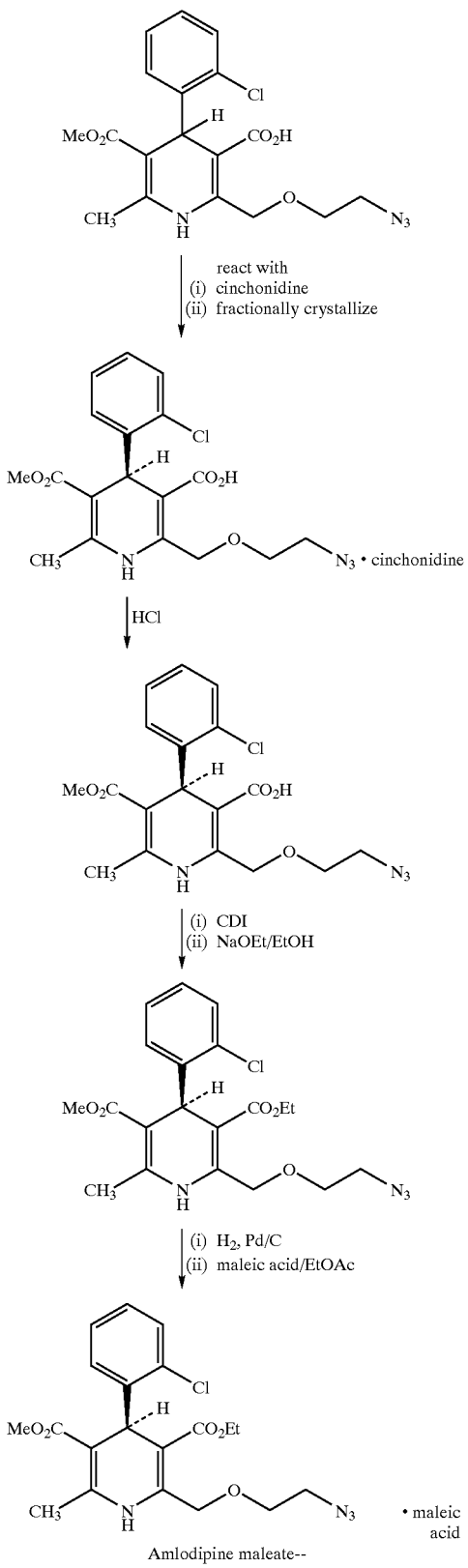

Amlodipine maleate--

The racemic acid 1 is converted to its cinchonidine salts in methanol solution. Upon dilution with water and standing at room temperature, a crystalline precipitate is formed which can be subsequently recrystallized to constant rotation to give the diastereomerically pure cinchonidine salt 2. Further, the mother liquids from the original crystallization can be reduced in volume and stirred at room temperature, e.g. overnight, to afford a fine precipitate which can also be recrystallized to give the diastereomerically pure cinchonidine salt 2. The cinchonidine salt 2 is partitioned between ethyl acetate and dilute hydrochloric acid to liberate the acid 3. The acid 3 is then esterified using carbonyldimidazole (CDI) in near-quantitative yield by forming an imidazolide and decomposing the imidazolide with ethanolic sodium ethoxide to give 4. The azido group in 4 can then be cleanly reduced to amino by catalytic hydrogenation, giving optically pure amlodipine, which is most conveniently isolated as the salt of an acid, e.g. as the maleate 5.

The magnitude of a prophylactic or therapeutic dose of (−) amlodipine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.01 mg. to about 100.0 mg. Preferably, a daily dose range should be between about 0.5 mg to about 20.0 mg. while most preferably, a daily dose range should be between about 0.5 mg to about 10 mg. In managing the patient, the therapy should be initiated at a lower dose, perhaps about 0.025 mg to about 2.5 mg and increased up to about 20 mg or higher depending on the patient's global response. It is further recommended that children and patients over 65 years, and those with impaired renal or hepatic function, initially receive low doses, and that they be titrated based on global response and blood level. It may be necessary to use dosages outside these ranges in some cases.

The various terms, "an amount sufficient to alleviate hypertension but insufficient to cause said adverse effects, "an amount sufficient to alleviate said condition but insufficient to cause said adverse effects" wherein said condition is angina; and "an amount sufficient to alleviate said condition but insufficient to cause said adverse effects" wherein said condition includes but is not limited to cerebral ischemia, cerebral disorders, arrhythmias, cardiac hypertrophy, coronary vasospasm, myocardial infarction, renal impairment and acute renal failure are encompassed by the above described dosage amounts and dose frequency schedule.

Any suitable route of administration may be employed for providing the patient with an effective dosage of (−) amlodipine. For example, oral, rectal, parenteral, transdermal, subcutaneous, intramuscular, and the like may be employed. Dosage forms include tablets, troches, dispersions, suspensions, solutions, capsules, patches, and the like.

The pharmaceutical compositions of the present invention comprise (−) amlodipine as active ingredient, or a pharmaceutically acceptable salt thereof, and may also contain a pharmaceutically acceptable carrier, and optionally, other therapeutic ingredients.

The term "pharmaceutically acceptable salts" refers to salts prepared from pharmaceutically acceptable non-toxic acids including inorganic acids and organic acids.

Since the compound of the present invention is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. (See Campbell, S. F. et al., U.S. Pat. No. 4,806,557.)

The compositions include compositions suitable for oral, rectal and parenteral (including subcutaneous, intramuscular, and intravenous) administration, although the most suitable route in any given case will depend on the nature and severity of the condition being treated. The most preferred route of the present invention is the oral route. The compositions may be conveniently presented in unit dosage form, and prepared by any of the methods well known in the art of pharmacy.

In the case where an oral composition is employed, a suitable dosage range for use is from about 0.01 mg. to about 100.0 mg. total daily dose, given as a once daily administration in the morning or in divided doses if required. Preferably, a dose range of between about 0.5 mg to about 20.0 mg is given as a once daily administration or in divided doses if required, and most preferably a dose range of from between about 0.5 mg to about 10.0 mg is given as a once daily administration or in divided doses if required. Patients may be upward titrated from below to within this dose range to a satisfactory control of symptoms or blood pressure as appropriate.

In practical use, (−) amlodipine can be combined as the active ingredient in intimate admixture with a pharmaceutical carrier according to conventional pharmaceutical compounding techniques. The carrier may take a wide variety of forms depending on the form of the preparation desired for administration, e.g., oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets) with the oral solid preparations being preferred over the oral liquid preparations. The most preferred oral solid preparation is tablets.

Because of their ease of administration, tablets and capsules represent the most advantageous; oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions of the present; invention suitable for oral administration may be presented as discrete units such as capsules, cachets, or tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, and/or surface active or dispersing agent. Molded tablets may be made by molding in a suitable machine a mixture of the powdered compound moistened with an inert liquid diluent. Desirably, each tablet contains from about 0.01 mg to about 50 mg of the active ingredient, and each cachet or capsule contains from about 0.5 mg to about 50 mg of the active ingredient, (−) amlodipine. Most preferably, the tablet, cachet or capsule contains either one of three dosages, 0.5 mg, 2.5 mg and 5.0 mg (as scored tablets, the preferable dose form) of the active ingredient.

The invention is further defined by reference to the following examples describing in detail the testing and preparation of the compositions of the present invention. It will be apparent to those skilled in the art, that many modifications, both to materials and methods, may be practiced without departing from the purpose and interest of this invention.

4. EXAMPLES

4.1. Example 1

Vascular Selectivity Studies

The relative potency of optically pure (−) amlodipine and racemic amlodipine as calcium channel antagonists and negative inotropic agents are determined by a pharmacological study. Evaluation of these compounds and others in in vitro test systems provide results, from which the vascular selectivity of a particular compound can be assessed. Calcium channel antagonist activity of the compounds as a function of their molar concentration can be evaluated by measuring their inhibition of the calcium-induced contraction of strips of rat aorta immersed in a bath of Krebs-Henseleit buffer containing 45 mM $K^+$ and no $Ca^{2+}$. In the presence of various concentrations of the antagonists, inhibition would occur in the contraction of this isolated tissue preparation in response to the addition of calcium chloride. Antagonists may be compared by examining the molar concentration of compounds inhibiting the calcium-induced contraction by 50%.

As an index of cardiac depression, negative inotropic activity may be comparably assessed using isolated heart preparations of adult rats. The tissues are prepared and perfused in vitro with Krebs-Henseleit buffer solution, with the activity of the calcium channel antagonists evaluated as a function of their concentration. The compounds are tested for their ability to alter cardiac contraction. Relative potency is calculated from the $IC_{25}$ values of the compounds, i.e., the concentration required to depress contraction by 25%.

4.2. Example 2

Radioligand Binding Studies

Hind limb skeletal muscles from rats or guinea pigs are minced and homogenized. After filtration and repeated centrifugation, the pellet is homogenized and diluted in a Tris buffer to a protein concentration of 1–3 mg/ml. Volumes of this suspension containing 3–10 μg protein are incubated in the presence of a fixed concentration of 0.2 to 0.5 nM (+)-[$^3$H]-isradipine or a similar radioactive ligand and increasing concentrations of racemic amlodipine, (−) amlodipine or (+) amlodipine. After 1 hour incubation, the bound and free radioactivity is measured in a scintillation counter and the affinity of the test compounds to the receptors is calculated.

4.3. Example 3

Effects on Coronary Vascular Resistance in the Guinea Pig Langendorff Heart Preparation Male guinea pigs weighing between 400 and 450 g are killed by cervical dislocation. The hearts are removed and perfused with Krebs-Henseleit solution at constant pressure (60 cm water) by means of retrograde cannulation of the aorta in a Langendorff apparatus. The Krebs-Henseleit solution, consisting of 118.0 mM NaCl, 4.7 mM KCl, 5.5 mM $CaCl_2$, 1.2 nM $MgSO_4$, 25.0 mM $NaHCO_3$ and 5.0 mM glucose, is prewarmed to 37° C. and gassed with a mixture of 95% oxygen/5% carbon dioxide. A balloon catheter connected to a pressure transducer is placed in the left ventricle via the left atrium and is preloaded to a pressure of 40 mm Hg. Coronary perfusate flow is measured continuously, and changes in heart rate and left ventricular contractility are also monitored continuously.

Each experiment consists of a 30 minute equilibrium period during which coronary flow is stabilized at 9–12 ml/min. Following this period, a vasoconstrictor is injected 3 times at 40 minute intervals into the cannulated aorta. This dose of U-46619 (9,11-methanoepoxy-$PGH_2$) evokes approximately a 75% decrease in coronary flow within 30–40 sec, and the effect is fully reversible after 20–25 min continuous perfusion. Racemic amlodipine, (−) amlodipine or (+) amlodipine dissolved in dimethyl sulfoxide or the vehicle are injected in increasing concentrations prior to further U-46619 injections.

The mean decrease in coronary flow obtained with three consecutive injections of U-46619 in the absence of the test substance is taken to be 100% and the percent inhibition of this effect in the presence of increasing concentrations of the test drugs is calculated. Complete individual dose-response curves for each test drug are generated in five hearts, enabling the calculation of the dose for the half-maximal antivasoconstrictor effect ($ID_{50}$).

4.4. Example 4

Antihypertensive Efficacy in Spontaneously Hypertensive Rats

Male spontaneously hypertensive rats (300–350 g) are anesthetized, and polyethylene catheters are implanted in the abdominal aorta via a femoral artery, and in the abdominal vena cava via a femoral vein. The arterial catheters are connected to pressure transducers by means of an intraflow device, flushing the catheters with 3 ml/hr. Mean arterial pressures are derived electronically from the blood pressure wave. Mean pretreatment values of mean arterial pressure are in the range of 160–220 mm Hg. Doses of racemic amlodipine, (−) amlodipine and (+) amlodipine, or of the solvent vehicle, are injected into the venous catheter. Responses in mean arterial pressure to the respective drug or solvent are registered and the relative potencies of the test compounds are calculated.

4.5. Example 5

Cardiovascular

Calcium Antagonism, Guinea Pig Ileum (In Vitro):

Test substance (3 μg/ml) inhibition of the contractile response of the $K^+$-depolarized isolated guinea pig ileal segment, bathed in Ca-free physiological salt solution at 37° C., to added calcium (20 μg/ml of CaCl), indicates calcium antagonist activity.

Reference Agents ($ED_{100}$,μg/ml):

| atropine | >2 | isoxuprine | 4 |
| cinnazrizine | 1 | mepyramine | >5 |
| cyproheptadine | 0.025 | nifedipine | 0.001 |
| diltiazem | 0.01 | papaverine | 4 |
| diphenhydramine | 1 | promethazine | 0.25 |
| flunarizine | 0.1 | propranolol | 4 |
| ipratropium bromide | >2 | verapamil | 0.01 |

4.6. Example 6

Studies on Insulin Resistance

Insulin is a hormone that activates various biochemical processes in the body, the most well known being facilitation of glucose transport over cell membranes and activation of cell growth. The development of insulin resistance is common both in diabetics and nondiabetics, but it is only the glucose transport system that develops resistance to insulin. To compensate for the impaired glucose transport, the normal body produces more insulin and the diabetic patient has to inject higher doses of insulin. Since insulin also is a growth hormone, the increased insulin concentration induces an accelerated growth of atherosclerotic lesions and increased risk for cardiovascular morbidity and mortality.

The present studies are performed in old, spontaneously hypertensive rats (SHRs), which are known to develop insulin resistance. Racemic amlodipine, (−) amlodipine, and (+) amlodipine are studied for their effects on glucose transport, insulin plasma concentration and arterial blood pressure.

Prior to receiving vehicle or test compound, basal measurements of the following parameters are made: (1) systolic blood pressure (measured via tail cuff occlusion); (2) fasting levels of plasma insulin and triglycerides; and (3) glucose tolerance.

The SHRs receive vehicle or test compound via oral gavage once or twice daily for two or four weeks. Measurements of blood pressure, circulating insulin and triglycerides, and glucose clearance are made following two (and four) weeks of drug administration. Any changes in insulin resistance resulting from the drug treatment are evident as changes in the ratio of plasma glucose/plasma insulin levels and from the glucose tolerance tests.

4.7. Example 7

Oral Formulation

| | Capsules: | | |
|---|---|---|---|
| | Quantity per capsule, in mg. | | |
| Formula | A | B | C |
| Active ingredient (-) Amlodipine | 0.5 | 2.5 | 5.0 |
| Lactose | 83.5 | 81.5 | 79.0 |
| Corn Starch | 15.0 | 15.0 | 15.0 |
| Magnesium Stearate | 1.0 | 1.0 | 1.0 |
| Compression weight | 100.0 | 100.0 | 100.0 |

The active ingredient, (−) amlodipine, lactose, and corn starch are blended until uniform; then the magnesium stearate is blended into the resulting powder. The resulting mixture is encapsulated into suitably sized two-piece hard gelatin capsules.

4.8. Example 8

Oral Formulation

| | Tablets | | |
|---|---|---|---|
| | Quantity per tablet in Gm. | | |
| Formula | A | B | C |
| Active ingredient (-) Amlodipine | 0.5 | 2.5 | 5.0 |
| lactose BP | 183.0 | 181.0 | 178.5 |
| starch BP Pregelatinized Maize Starch BP | 15.0 | 15.0 | 15.0 |
| magnesium stearate | 1.5 | 1.5 | 1.5 |
| Compression Weight | 200.0 | 200.0 | 200.0 |

The active ingredient, (−) amlodipine, is sieved through a suitable sieve and blended with lactose, starch, and pregelatinized maize starch. Suitable volumes of purified water are added and the powders are granulated. After drying, the granules are screened and blended with the magnesium stearate. The granules are then compressed into tablets using 7 mm diameter of punches.

Tablets of other strengths may be prepared by altering the ratio of active ingredient to lactose or the compression weight and using punches to suit.

What is claimed is:

1. A method of eliciting an antihypertensive effect in a human, which comprises administering to a human in need thereof of a therapeutically effective amount of an acid addition salt of (−) amlodipine substantially free of its (+)stereoisomer.

2. The method of claim 1 wherein the acid addition salt of (−) amlodipine is a salt of benzoic acid.

3. The method of claim 1, wherein the acid addition salt of (−) amlodipine is a salt of benzoic acid.

4. The method of claim 1, wherein the acid addition salt of (−) amlodipine is a salt of camphorsulfonic acid.

5. The method of claim 1, wherein the acid addition salt of (−) amlodipine is a salt of citric acid.

6. The method of claim 1, wherein the acid addition salt of (−) amlodipine is a salt of ethenesulfonic acid.

7. The method of claim 1, wherein the acid addition salt of (−) amlodipine is a salt of fumaric acid.

8. The method of claim 1, wherein the acid addition salt of (−) amlodipine is a salt of gluconic acid.

9. The method of claim 1, wherein the acid addition salt of (−) amlodipine is a salt of glutamic acid.

10. The method of claim 1, wherein the acid addition salt of (−) amlodipine is a salt of hydrobromic acid.

11. The method of claim 1, wherein the acid addition salt of (−) amlodipine is a salt of hydrochloric acid.

12. The method of claim 1, wherein the acid addition salt of (−) amlodipine is a salt of isethionic acid.

13. The method of claim 1, wherein the acid addition salt of (−) amlodipine is a salt of lactic acid.

14. The method of claim 1, wherein the acid addition salt of (−) amlodipine is a salt of maleic acid.

15. The method of claim 1, wherein the acid addition salt of (−) amlodipine is a salt of malic acid.

16. The method of claim 1, wherein the acid addition salt of (−) amlodipine is a salt of mandelic acid.

17. The method of claim 1, wherein the acid addition salt of (−) amlodipine is a salt of methanesulfonic acid.

18. A The method of claim 1, wherein the acid addition salt of (−) amlodipine is a salt of mucic acid.

19. The method of claim 1, wherein the acid addition salt of (−) amlodipine is a salt of nitric acid.

20. The method of claim 1, wherein the acid addition salt of (−) amlodipine is a salt of pamoic acid.

21. The method of claim 1, wherein the acid addition salt of (−) amlodipine is a salt of pantothenic acid.

22. The method of claim 1, wherein the acid addition salt of (−) amlodipine is a salt of phosphoric acid.

23. The method of claim 1 wherein the acid addition salt of (−) amlodipine is a salt of succinic acid.

24. The method of claim 1, wherein the acid addition salt of (−) amlodipine is a salt of sulfuric acid.

25. The method of claim 1, wherein the acid addition salt of (−) amlodipine is a salt of tartaric acid.

26. The method of claim 1, wherein the acid addition salt of (−) amlodipine is a salt of toluenesulfonic acid.

27. A method of treating angina in a human, which comprises administering to a human in need thereof a therapeutically effective amount of an acid addition salt of (−) amlodipine substantially free of its (+) stereoisomer.

28. The method of claim 27, wherein the acid addition salt of (−) amlodipine is a salt of acetic acid.

29. The method of claim 27, wherein the acid addition salt of (−) amlodipine is a salt of benzoic acid.

30. The method of claim 27, wherein the acid addition salt of (−) amlodipine is a salt of camphorsulfonic acid.

31. The method of claim 27, wherein the acid addition salt of (−) amlodipine is a salt of citric acid.

32. The method of claim 27, wherein the acid addition salt of (−) amlodipine is a salt of ethenesulfonic acid.

33. The method of claim 27, wherein the acid addition salt of (−) amlodipine is a salt of fumaric acid.

34. The method of claim 27, wherein the acid addition salt of (−) amlodipine is a salt of gluconic acid.

35. The method of claim 27, wherein the acid addition salt of (−) amlodipine is a salt of glutamic acid.

36. The method of claim 27, wherein the acid addition salt of (−) amlodipine is a salt of hydrobromic acid.

37. The method of claim 27, wherein the acid addition salt of (−) amlodipine is a salt of hydrochloric acid.

38. The method of claim 27, wherein the acid addition salt of (−) amlodipine is a salt of isethionic acid.

39. The method of claim 27, wherein the acid addition salt of (−) amlodipine is a salt of lactic acid.

40. The method of claim 27, wherein the acid addition salt of (−) amlodipine is a salt of maleic acid.

41. The method of claim 27, wherein the acid addition salt of (−) amlodipine is a salt of malic acid.

42. The method of claim 27, wherein the acid addition salt of (−) amlodipine is a salt of mandelic acid.

43. The method of claim 27, wherein the acid addition salt of (−) amlodipine is a salt of methanesulfonic acid.

44. The method of claim 27, wherein the acid addition salt of (−) amlodipine is a salt of mucic acid.

45. The method of claim 27, wherein the acid addition salt of (−) amlodipine is a salt of nitric acid.

46. The method of claim 27, wherein the acid addition salt of (−) amlodipine is a salt of pamoic acid.

47. The method of claim 27, wherein the acid addition salt of (−) amlodipine is a salt of pantothenic acid.

48. The method of claim 27, wherein the acid addition salt of (−) amlodipine is a salt of phosphoric acid.

49. The method of claim 27, wherein the acid addition salt of (−) amlodipine is a salt of succinic acid.

50. The method of claim 27, wherein the acid addition salt of (−) amlodipine is a salt of a sulfuric acid.

51. The method of claim 27, wherein the acid addition salt of (−) amlodipine is a salt of tartaric acid.

52. The method of claim 27, wherein the acid addition salt of (−) amlodipine is a salt of p-toluenesulfonic acid.

\* \* \* \* \*

UNITED STATES PATENT AND TRADEMARK OFFICE
CERTIFICATE OF CORRECTION

PATENT NO.    : 6,448,275 B2
DATED         : September 10, 2002
INVENTOR(S)   : James W. Young It is certified that error appears in the above-identified patent and that said Letters Patent is hereby corrected as shown below:

<u>Column 15,</u>
Line 61, replace "benzoic" with -- acetic --.

Signed and Sealed this

Twenty-sixth Day of November, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.     : 6,448,275 B2
DATED          : September 10, 2002
INVENTOR(S)    : James W. Young It is certified that error appears in the above-identified patent and that said Letters Patent is hereby corrected as shown below:

<u>Title page, Item [54] and Column 1, line 4,</u>
Replace "AMPLODIPINE" with -- AMLODIPINE --.

Signed and Sealed this

Nineteenth Day of August, 2003

JAMES E. ROGAN
*Director of the United States Patent and Trademark Office*